United States Patent
Breedveld

(10) Patent No.: US 7,789,824 B2
(45) Date of Patent: Sep. 7, 2010

(54) INSTRUMENT COMPRISING A CABLE OR TUBE PROVIDED WITH A PROPULSION DEVICE

(75) Inventor: Paulus Breedveld, Gouda (NL)

(73) Assignee: Technische Universiteit Delft, Delft (NL)

( * ) Notice: Subject to any disclaimer, the term of this patent is extended or adjusted under 35 U.S.C. 154(b) by 755 days.

(21) Appl. No.: 11/674,867

(22) Filed: Feb. 14, 2007

(65) Prior Publication Data

US 2007/0208299 A1 Sep. 6, 2007

Related U.S. Application Data

(63) Continuation-in-part of application No. PCT/NL2005/000564, filed on Aug. 1, 2005.

(30) Foreign Application Priority Data

Aug. 19, 2004 (NL) .................... 1026884

(51) Int. Cl.
- A61B 1/04 (2006.01)
- A61M 31/00 (2006.01)
- A61M 37/00 (2006.01)

(52) U.S. Cl. .............. 600/114; 600/115; 600/116; 604/103.07; 604/103.08

(58) Field of Classification Search .......... 600/114, 600/115–116; 604/103.05, 103.07, 103.08, 604/103.09, 103.12, 105, 109, 202; 606/159
See application file for complete search history.

(56) References Cited

U.S. PATENT DOCUMENTS

| | | | |
|---|---|---|---|
| 3,895,637 A | 7/1975 | Choy | |
| 4,676,228 A | 6/1987 | Krasner et al. | |
| 4,690,131 A | 9/1987 | Lyddy et al. | |
| 5,053,008 A * | 10/1991 | Bajaj | 604/104 |
| 5,102,415 A * | 4/1992 | Guenther et al. | 606/159 |
| 5,337,732 A | 8/1994 | Grundfest et al. | |
| 5,398,670 A | 3/1995 | Ortiz et al. | |
| 5,454,364 A | 10/1995 | Kruger | |
| 5,562,601 A | 10/1996 | Takada | |
| 5,749,883 A * | 5/1998 | Halpern | 606/159 |
| 5,906,591 A | 5/1999 | Dario et al. | |
| 5,967,984 A | 10/1999 | Chu et al. | |
| 6,071,234 A * | 6/2000 | Takada | 600/114 |
| 6,224,544 B1 | 5/2001 | Takada | |
| 6,231,544 B1 * | 5/2001 | Tsugita et al. | 604/104 |
| 6,309,346 B1 | 10/2001 | Farhadi | |
| 6,648,814 B2 | 11/2003 | Kim et al. | |

(Continued)

FOREIGN PATENT DOCUMENTS

WO   WO 2004050392   6/2004

*Primary Examiner*—Linda C Dvorak
*Assistant Examiner*—Alireza Nia
(74) *Attorney, Agent, or Firm*—Jeffrey D. Myers; Jacques van Breda; Peacock Myers, P.C.

(57) ABSTRACT

An instrument comprising a cable or tube, at a distal end of which a propulsion device is provided for moving the cable or tube in a hollow space, the propulsion device being shaped like a donut lying in a plane at right angles to the longitudinal direction of the cable or tube, wherein the donut-shaped propulsion device is, at least in part, externally delimited by at least one wire gauze that is rotatable about a closed axis of the donut body, which axis lies in the plane of the donut.

9 Claims, 5 Drawing Sheets

U.S. PATENT DOCUMENTS

| | | |
|---|---|---|
| 6,695,771 B2 | 2/2004 | Takada |
| 7,011,672 B2 * | 3/2006 | Barbut et al. ............... 606/200 |
| 2002/0040221 A1 | 4/2002 | Paddock et al. |
| 2002/0123664 A1 | 9/2002 | Mitsumori |
| 2003/0065250 A1 | 4/2003 | Chiel et al. |
| 2004/0107004 A1 | 6/2004 | Levine et al. |
| 2005/0059925 A1 * | 3/2005 | Maginot et al. ............... 604/43 |

* cited by examiner

INSTRUMENT COMPRISING A CABLE OR TUBE PROVIDED WITH A PROPULSION DEVICE

CROSS-REFERENCE TO RELATED APPLICATIONS

This application is a continuation application of International Serial No. PCT/NL2005/000564, entitled "Instrument Comprising a Cable or Tube Provided with a Propulsion Device", filed on Aug. 1, 2005, and the specification and claims thereof are incorporated herein by reference.

This application, Serial No. PCT/NL2005/000564, claims priority to and the benefit of the filing of Netherlands Patent Application Serial No. 1026884, entitled "Instrument Comprising a Cable or Tube Provided with a Propulsion Device", filed on Aug. 19, 2004, and the specification and claims thereof are incorporated herein by reference.

STATEMENT REGARDING FEDERALLY SPONSORED RESEARCH OR DEVELOPMENT

Not Applicable.

The research that has resulted in the present invention has been made possible by a grant from the Royal Dutch Academy of Sciences.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

Instrument comprising a cable or tube provided with a propulsion device

The invention relates to an instrument comprising a cable or tube, and a propulsion device for moving the cable or tube in a hollow space. Such an instrument may be used for moving in industrial tubular constructions such as pipes, tubes or sewer systems. However, such an instrument is also useful in medical applications when the hollow space is formed by esophagus, stomach, small intestine or blood vessels. Others to be mentioned are the bladder, windpipe, large intestine, duodenum, auditory duct and nose. Other possible spaces are the abdominal cavity, chest cavity, nasal and sinus cavities, the epidural cavity, hollow bones, etc.

Hereinafter the instrument of the invention will be further elucidated by way of its use as colonoscope. It is explicitly remarked, however, that the invention is not limited to just such a medical instrument but that all possible instruments as indicated above fall within the scope of the invention.

Patients suffering from intestinal complaints are usually subjected to a colonoscopy. With this examination, the patient is first given a laxative liquid to drink, after which the large intestine evacuates. Then a 1.5 meter long thin tube is introduced. On the tip of the known colonoscope used for this purpose a camera is provided with a light source and a duct through which an instrument can be introduced into the intestine. In view of the possibility of complications arising during anesthesia, a colonoscopy is in principle performed while the patient is conscious.

A drawback of the colonoscope is that the tip is introduced from a distance, via a long thin tube. There is a possibility that the tip catches behind projections in the intestinal wall so that pushing forces develop that cause the tube to buckle. When the tube buckles, considerable forces are exerted on the intestinal wall, causing cramp and pain. In the worst case the intestinal wall may become perforated, which may lead to life-threatening situations.

2. Description of Related Art

The prior art discloses various alternative solutions to reduce the problems with moving the colonoscope in the large intestine of the patient. Examples are sliding systems that work with balloons as shown in U.S. Pat. No. 3,895,637; U.S. Pat. No. 4,676,228; U.S. Pat. No. 4,690,131; U.S. Pat. No. 5,337,732; U.S. Pat. No. 5,398,670; and U.S. Pat. No. 5,454,364. Other known systems are embodied with suction cups, see for example U.S. Pat. No. 5,906,591 and U.S. Pat. No. 6,309,346 BI; with wheels, see U.S. Pat. No. 6,648,814 B2, or with belts extending over the length of the colonoscope, see U.S. Pat. No. 6,695,771; U.S. Pat. No. 5,562,601; U.S. Pat. No. 6,071,234; and U.S. Pat. No. 6,224,544.

BRIEF SUMMARY OF THE INVENTION

The problem with these known systems is that due to the intestinal wall of the large intestine being provided with a mucous layer, they are unable to gain a satisfactory grip on the intestinal wall.

It is the object of the invention to provide an instrument of the kind expressed in the preamble, with which an improved propulsion in a hollow space can be realized, so as to render this instrument especially useful for medical applications in which the possibility of gaining sufficient grip on the walls of the hollow space is limited.

To this end the instrument is according to the invention characterized in that the propulsion device substantially has the shape of a donut lying in a plane at right angles to the longitudinal direction of the cable or tube, wherein the donut-shaped propulsion device is, at least in part, externally delimited by at least one wire gauze that is rotatable about a closed axis of the donut body, which axis lies in the plane of the donut. Although a donut-shape is usually understood to represent a round cyclotron-like shape, within the scope of the invention this also includes a less perfectly round shape. Through compression, the propulsion device may also assume a square or triangular shape with rounded corners, when, viewed from above.

This completely novel approach proposed according to the invention provides a propulsion device affording sufficient friction between the propulsion device and the wall of the hollow space, in particular the wall of the large intestine. This is assisted by the wire gauze that cuts through the mucous layer covering the wall and that thus, while it is rolled along the wall, is able to produce an adequate traction with respect to the intestinal wall.

It should furthermore be noted that possibilities existing within the scope of the invention include the use of more than one donut-shaped propulsion device. Similarly, the instrument may be embodied such that it is suitable for autonomic locomotion. To this end the propulsion device may be provided with one or several motors.

In a further aspect of the invention, it is desirable for the at least one wire gauze forming the donut to be fastened to the cable or tube by adjustable arms. In this embodiment, the adjustable arms may serve for adjusting the diameter of the donut in order to accommodate the various inside diameters that the hollow space may have while the instrument is moved through it.

A first suitable embodiment in which this may be realized is characterized, in that the adjustable arms are embodied as traction wires coupled to an axis or axes of the wire gauze, and springs surrounding these traction wires and extending between the cable or tube on the one side and the axis or axes of the wire gauze on the other side. Through the interaction of the traction wires and the springs provided around these traction wires, the diameter of the wire gauze can be simply adjusted by slackening or tightening the traction wires.

An alternative embodiment in which the diameter adjustment of the donut of the wire gauze can be realized is characterized, in that the cable or tube is provided with a sleeve, to which sleeve first ends of the arms are hingingly fastened, and in that opposite to the first ends, second ends of the arms are coupled with the at least one wire gauze. How this works will be explained in more detail in the description of the Figure following below.

It is actually conceivable that in order to start the at least one wire gauze rotating, a drive is provided, for example, in the interior of this wire gauze. Especially in the context of medical applications, it is however desirable for the at least one wire gauze to be coupled with a drive that is located at a proximal end of the cable or tube; that is to say extracorporeally. This embodiment is articularly suitable for an application in which the arrangement of drive and accessories is fixed and permanent while the part inserted into the patient is embodied as non-durable part.

The coupling between the drive and the at least one wire gauze may preferably be realized by using traction wires extending in or along the cable or tube and externally guided around the donut-shaped propulsion device. The traction wires thus run around the outer circumference of the donut while being in frictional contact with the same such that the adjustment of the traction wires results in a corresponding rotation of the donut about the closed axis of the donut body, which lies in the plane of the donut.

In order to realize a buckle-free drive of the propulsion device despite the flexibility of the cable or tube, it is advisable to guide the traction wires through Bowden cables.

It is further advantageous for the at least one wire gauze to be torsion-rigid about its body axis that lies in the plane of the donut.

The at least one wire gauze of the propulsion device is preferably embodied as interwoven wires selected from the group comprising metal wires, for example, spring steel, plastic wires, nitinol wires.

In particular for medical purposes, the instrument is suitably embodied with a stent in the form of wire gauze.

Hereinafter the invention will be further elucidated by way of an exemplary embodiment and with reference to the drawing, which is not limiting with regard to the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

The drawing shows in.

Similar parts in the figures carry the same reference numerals.

DETAILED DESCRIPTION OF THE INVENTION

Figure 1:
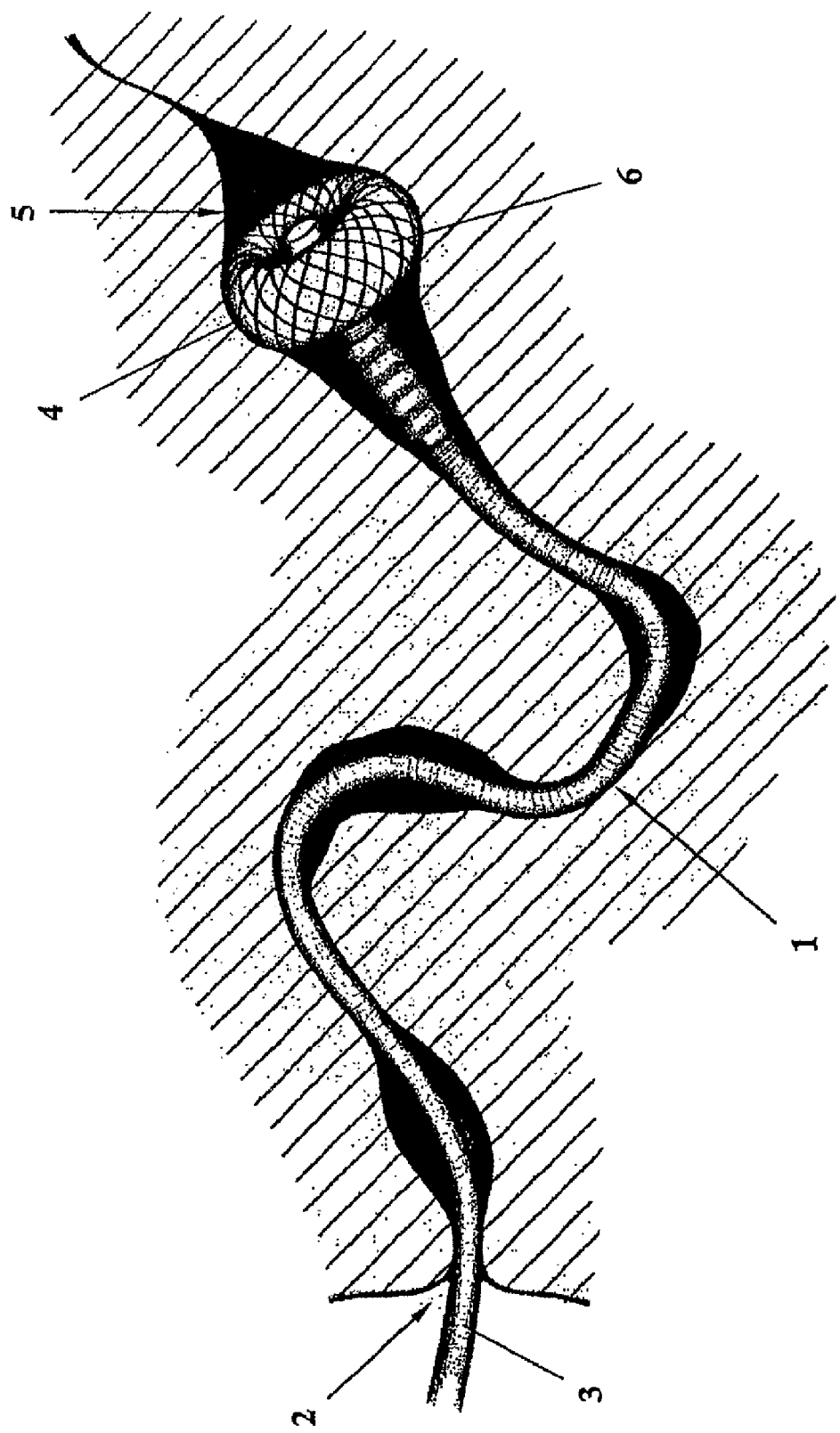
FIG. 1, an instrument according to the invention embodied as colonoscope, in the inserted situation.

Referring first to FIG. 1, an instrument is shown carrying reference numeral 1, which is embodied as colonoscope.

The colonoscope 1 is inserted via an anus 2 and is provided with a cable 3 having a propulsion device 4 at its cross-cut, distal end. As clearly shown in FIG. 1, the diameter of the instrument 1 at this propulsion device 4 is larger than the diameter of the cable or tube 3, and the diameter of the large intestine 5 automatically adapts to this larger diameter.

As further clearly shown in FIG. 1, the propulsion device 4 is formed like a donut that lies in a plane oriented at right angles to the longitudinal direction of the cable or tube 3 in the immediate vicinity, and the donut-shaped propulsion device is externally delimited by a wire gauze 6. As will be explained hereinafter, this wire gauze 6 is rotatable about a closed axis of the donut body, which axis lies in the plane of the donut.

Figure 2:
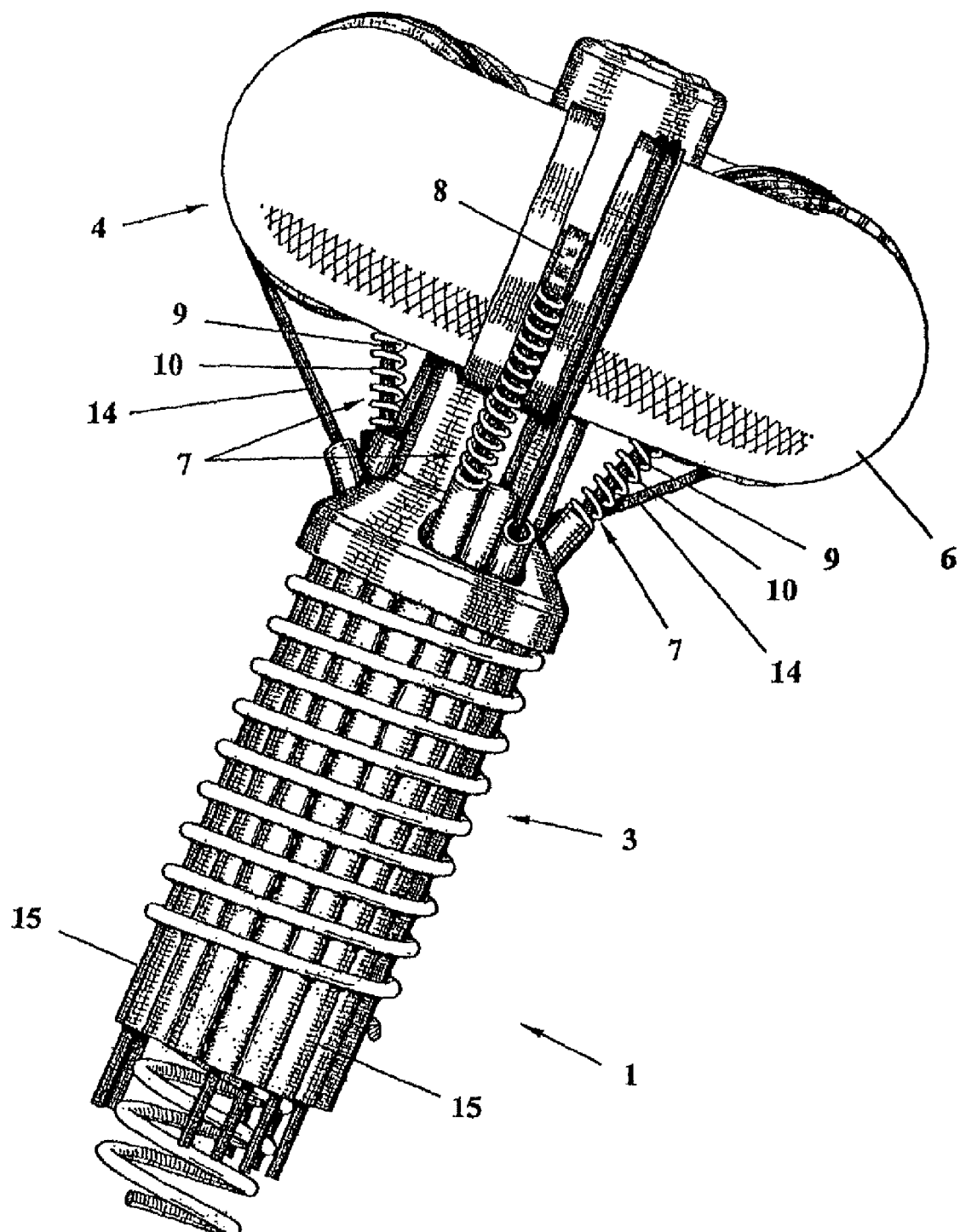
FIG. 2, a schematically represented side elevation of an end of the colonoscope shown in FIG. 1 in a first embodiment.

FIG. 2 shows the portion of the instrument 1 according to the invention that is located in the direct vicinity of the wire gauze 6 of the propulsion device 4. For the sake of simplicity, the wire gauze 6 is shown as solid surface in the above-described recognizable form of a donut. Via adjustable arms 7, this donut is fastened to the cable or tube 3.

Figure 3:
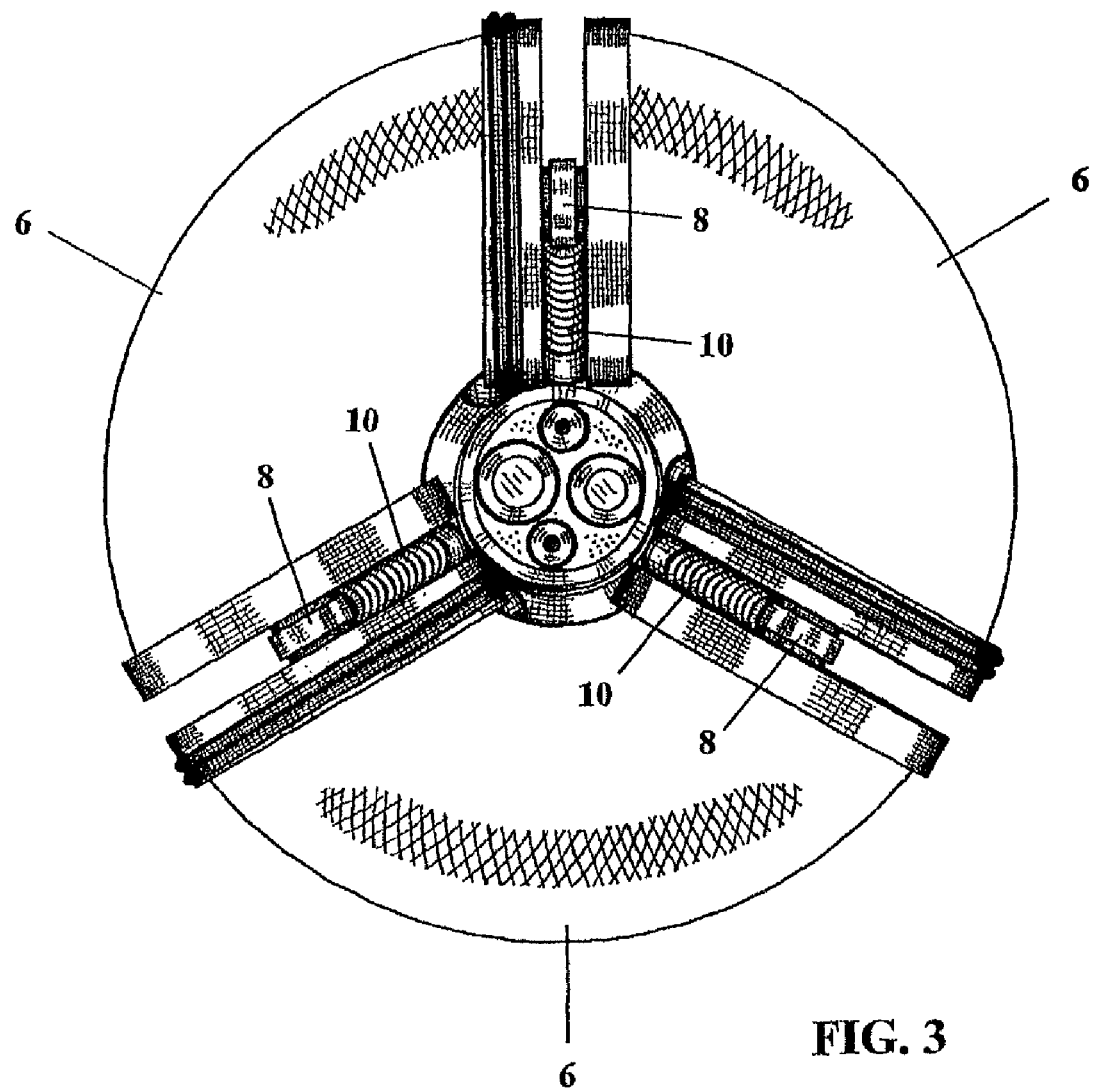
FIG. 3, a cross-sectional view of the partly shown colonoscope of FIG. 2.

The embodiment illustrated in FIG. 2 and FIG. 3 shows that these adjustable arms 7 are embodied as traction wires 9 coupled to an axis or axes 8 of the wire gauze 6, and springs 10 surrounding said traction wires 9, extending between the cable or tube 3 on the one side and the axis or axes 8 of the wire gauze 6 on the other side. FIG. 3, illustrating a cross-sectional view of the end of the colonoscope, clearly shows in this embodiment that the axes 8 form connecting elements between three separate wire gauzes 6. The FIGS. 2 and 3 show the wire gauzes 6 in a configuration in which they have a smallest diameter. Slackening of the traction wires 9 releases the springs 10, allowing the diameter of the wire gauzes 6 that together form the propulsion device 4 to enlarge, so that this propulsion device is simply adaptable to variable diameters of the wall of the hollow space accommodating the propulsion device 4.

Figure 4:
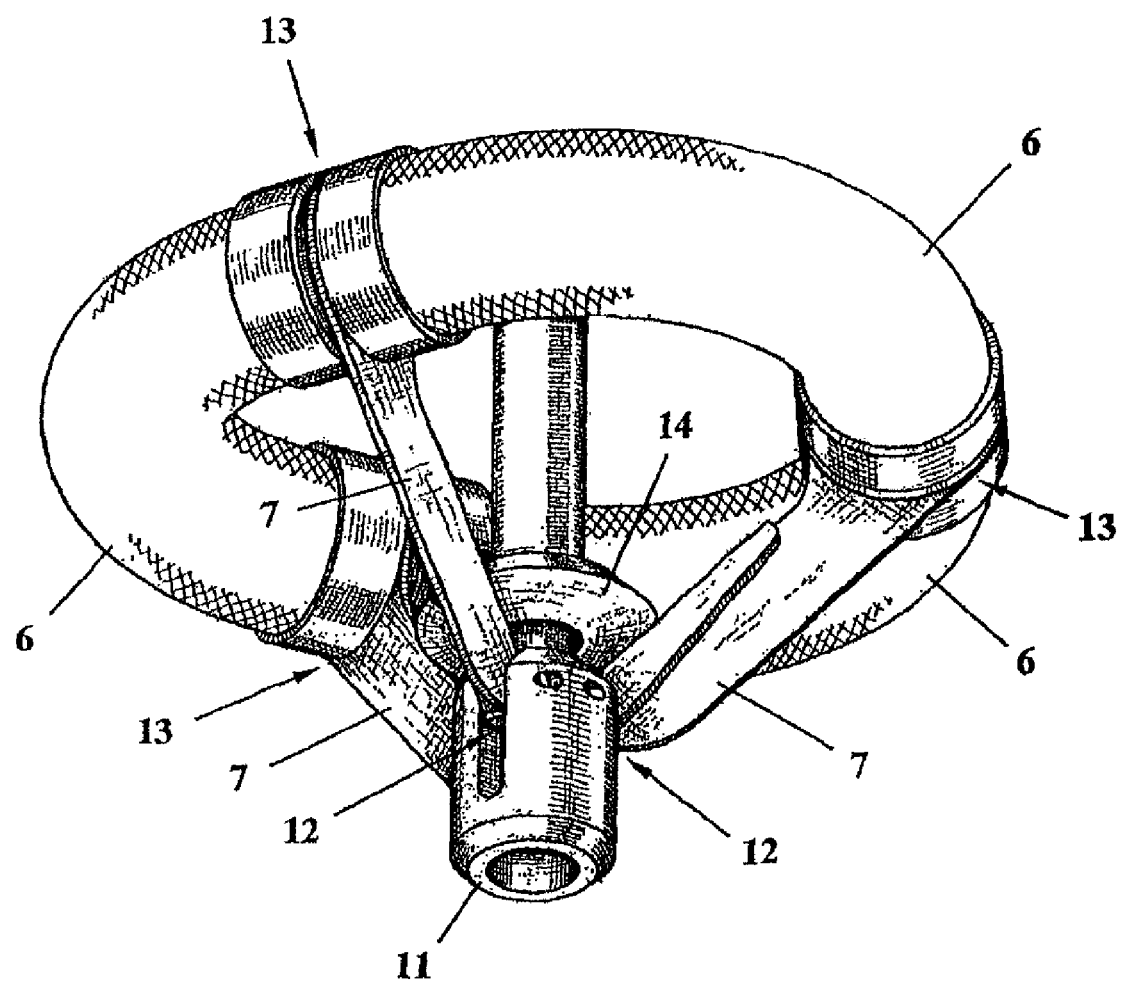
FIG. 4, a detail of a second embodiment of the cross-sectional end of the colonoscope shown in FIG. 1 in a first position.
Figure 5:
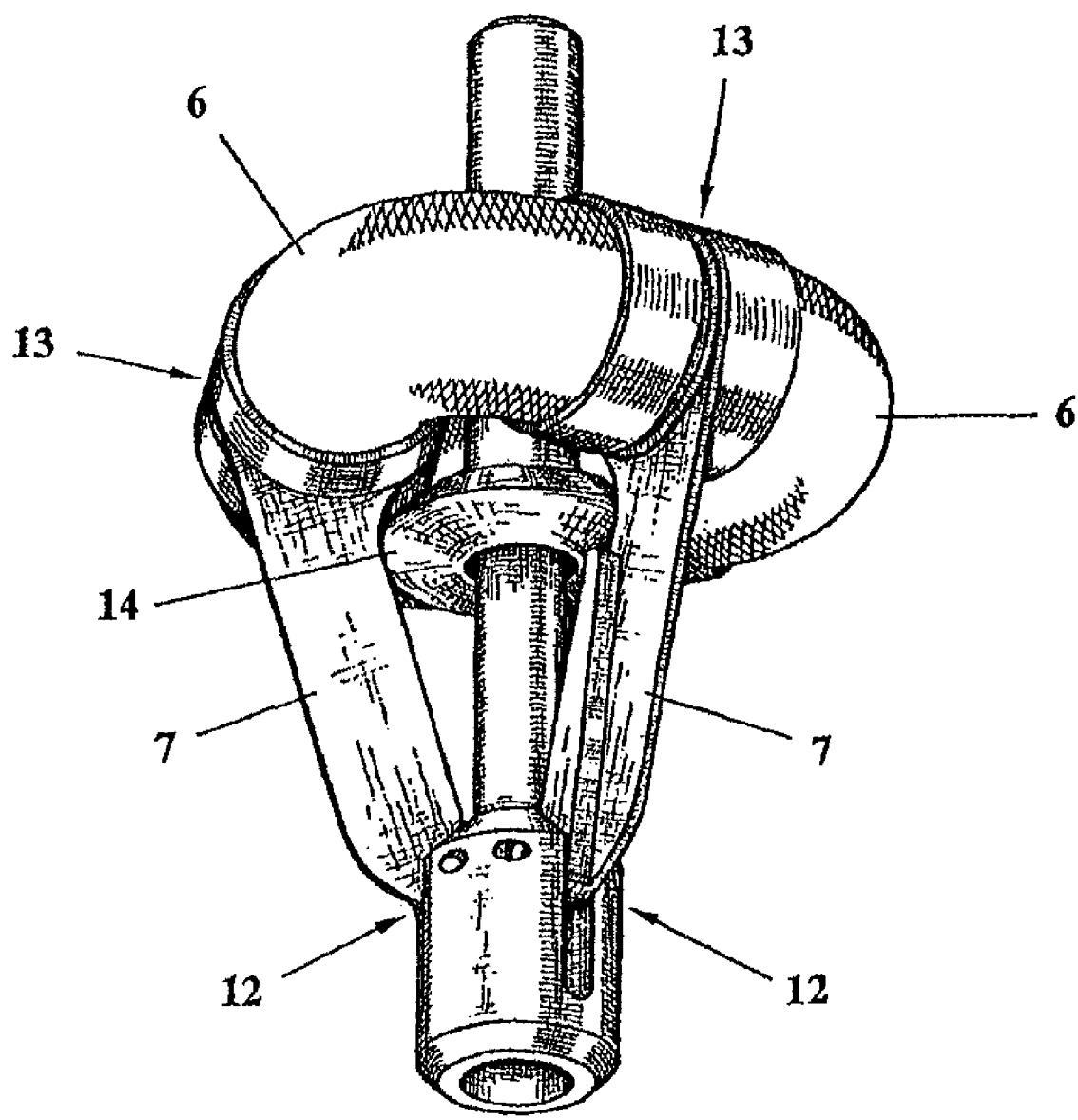
FIG. 5, the detail of an end of the colonoscope shown in FIG. 4 in a second position.

FIGS. 4 and 5 show an alternative embodiment of the propulsion device 4 with an enlarged diameter (FIG. 4) and a small diameter (FIG. 5) respectively, in which the diameter adjustment is realized in a different manner. In this embodiment the cable or tube, which is actually not shown in FIGS. 4 and 5, is provided with a sleeve 11 permanently mounted thereon, to which sleeve 11 first ends 12 of the arms 7 are hingingly fastened and wherein second ends 13 located opposite the first ends 12 of the arms 7 are coupled with the at least one wire gauze 6. Adjustment of the arms 7 between the enlarged diameter (FIG. 4) and the small diameter (FIG. 5) takes place by adjusting a movable second sleeve 14 adjacent the arms 7. This embodiment also is provided with three separate wire gauzes 6. Actually, this number may be varied as required. It should be noted that for the sake of clarity the traction wires for driving the wire gauze 6 shown in FIG. 2 and which will be discussed below, are not shown in the embodiment in FIGS. 4 and 5.

Another aspect of the invention relates to the fact that the at least one wire gauze 6 is or may be coupled to a drive located at a proximal end of the cable or tube 3. That is to say, in the illustrated application of a colonoscope the drive is located extracorporeally. The manner in which this may be realized is quite obvious to the person skilled in the art so that a further elucidation by way of the drawing may be dispensed with.

When the drive is provided at a proximal end as mentioned above, it is advantageous that the at least one wire gauze 6 be coupled with that drive via traction wires 14 running in or along the cable or tube 3 and guided externally around the donut-shaped propulsion device 4. This is clearly shown in FIG. 2. As also shown in this FIG. 2, it is advantageous for the traction wires 14 to run through Bowden cables 15.

As will be obvious from the above, the instrument according to the invention may be varied in several ways without departing from the spirit of the invention as specified in the appended claims. For example, the three separate wire gauzes 6 may be provided with an individual drive as shown in FIG. 3 and FIG. 4, such that adapting the rotational speed of these wire gauzes 6 provides a simple manner for following bends in the hollow space to be examined.

The at least one wire gauze 6 may be made of various materials, although it is preferred to use a wire gauze made of metal wires. It is very practical to use a stent as wire gauze, especially when using the instrument according to the invention for medical applications.

The invention and the protective scope it merits are not limited to the above exemplary embodiment, but relate to all possible uses that may be assigned to the instrument as specified in the appended claims.

What is claimed is:

1. An instrument comprising a cable or tube, and at least one propulsion device for moving the cable or tube in a hollow space, wherein the propulsion device comprises a shape of a donut, said donut-shaped propulsion device comprising a ring that has a straight axis through its open center, wherein said ring lies in a plane perpendicular to the straight axis, wherein said cable or tube extends centrally along the straight axis into the immediate vicinity of said donut-shaped propulsion device such that the donut-shaped propulsion device lies in a plane at right angles to the longitudinal direction of the cable or tube, and wherein the donut-shaped propulsion device is, at least in part, externally delimited by at least one wire gauze that is rotatable about a closed axis of the donut-shaped propulsion device, wherein said closed axis lies in the plane of the donut, wherein the wire gauze externally delimiting the at least one donut-shaped propulsion device is fastened to the cable or tube by adjustable arms, wherein the cable or tube is provided with a sleeve, to which sleeve first ends of the arms are hingingly fastened, and in that opposite to the first ends, second ends of the arms are coupled with the at least one wire gauze, wherein the at least one wire gauze is coupled with a drive that is located at a proximal end of the cable or tube.

2. An instrument according to claim 1, wherein the propulsion device is provided with a motor drive.

3. An instrument according to claim 1, wherein the adjustable arms are embodied as traction wires coupled to an axis or axes of the wire gauze, and springs surrounding these traction wires and extending between the cable or tube on the one side and the axis or axes of the wire gauze on the other side.

4. An instrument according to claim 1, wherein the at least one wire gauze is coupled with the drive by traction wires extending in or along the cable or tube are externally guided around the donut-shaped propulsion device.

5. An instrument according to claim 4, wherein the traction wires are guided through Bowden cables.

6. An instrument according to claim 1, wherein the at least one wire gauze is torsion-rigid about its body axis that lies in the plane of the donut.

7. An instrument according to claim 1, wherein the wire gauze constitutes interwoven wires selected from the group comprising metal wires, plastic wires, nitinol wires.

8. An instrument according to claim 7, wherein the instrument serves for medical purposes, and in that the at least one wire gauze is a stent.

9. An instrument according to claim 8, wherein the instrument is a colonoscope.

* * * * *